United States Patent [19]

Hunter et al.

[11] Patent Number: 5,003,044

[45] Date of Patent: Mar. 26, 1991

[54] PEPTIDE INHIBITORS OF MOTOR NEURON ATTACHMENT TO S-LAMININ

[75] Inventors: Dale D. Hunter; Joshua R. Sanes; John P. Merlie, all of St. Louis; Steven P. Adams, St. Charles, all of Mo.

[73] Assignee: Washington University, St. Louis, Mo.

[21] Appl. No.: 382,606

[22] Filed: Jul. 19, 1989

[51] Int. Cl.$^5$ .......................... C07K 7/00; C07K 5/08; C07K 5/10
[52] U.S. Cl. .................................. 530/326; 530/327; 530/329; 530/330; 530/331
[58] Field of Search ............... 530/326, 327, 328, 329, 530/330, 331

[56] References Cited

PUBLICATIONS

Hunter et al., Cell, 1989, 59(5), pp. 905–913.
Hunter et al., Nature, 358, pp. 229–233 (1989).

Primary Examiner—Lester L. Lee
Assistant Examiner—Stephen B. Maebius
Attorney, Agent, or Firm—Scott J. Meyer; James W. Williams, Jr.

[57] ABSTRACT

Novel peptides having inhibitor activity toward the binding of motor neurons to s-laminin are disclosed which are selected from the group consisting of

AEKQLREQVGDQYQTVRALAE and fragments thereof containing the essential sequence LR

(1593)-IRGAVVDTKNTEQTLQQVQERMAGTEQSLNSASERARQLHALLEALKLKRAGNS
|—— M1 ——| |—— M2 ——| |—— M3 ——|

LAASTAEETAGSAQSRAREAEKQLREQVGDQYQTVRALAERKAEGVLAAQARAEQLRDEA
|—— M4 ——| |—— M5 ——| |—— M6 ——|

RGLLQAAQDKLQRLQELEGTYEENERELEVKAAQLDGLEARMRSVLQAINLQVQIYNTCQ
|—— M7 ——| |—— M8 ——| |—— M9 ——|

| | PEPTIDE | | $IC_{50}$ (μg/ml) |
|---|---|---|---|
| A | M5 | AEKQLREQVGDQYQTVRALAE | 30 |
| | M51 | AEKQLREQVGD | 20 |
| | M52 | QYQTVRALAE | >200 |
| | | | |
| | M511 | AEKQLR | >200 |
| B | M512 | KQLREQ | <100 |
| | M513 | LREQVG | <100 |
| | M53 | EQVGDQYQTV | >200 |
| | | | |
| | | LREQ | <100 |
| C | | LRE | 10 |
| | | LR | >200 |
| | | RE | >200 |

PEPTIDE INHIBITORS OF MOTOR NEURON ATTACHMENT TO S-LAMININ

BACKGROUND OF THE INVENTION

This invention relates to novel peptides and, more particularly, to short synthetic peptides that block cell attachment to s-laminin.

S-laminin is a ~190 kDa laminin-like glycoprotein that is concentrated in synaptic basal laminae. See Hunter et al, *Nature* 338, 229–234 (1989). S-laminin may play a role in the selective reinnervation of original synaptic sites and/or in the differentiation of axons into nerve terminals at these sites. This theory is supported by the homology of s-laminin to the β1 subunit of laminin, which is known to be a major neurite outgrowth-promoting component of basal laminae.

It has been previously reported that neurons from embryonic chick ciliary ganglia adhere to a recombinant protein that consists of the C-terminal 40% of s-laminin fused to a 10 amino acid fragment of a phage capsid protein. See Hunter et al., supra. However, the essential motor neuron-attachment site of s-laminin has not been identified or described heretofore.

BRIEF DESCRIPTION OF THE INVENTION

In accordance with the present invention novel synthetic peptides have been developed which are able to block cell attachment to s-laminin. As such, these peptides are capable of inhibiting the binding of motor neurons to s-laminin. These are short peptides which contain the essential tripeptide sequence, leucine-arginine-glutamic acid (LRE).

Although the LRE tripeptide sequence occurs in many large proteins, most of these occurrences are believed to be functionally insignificant, because the residues are buried, because the residues are in contexts that render them ineffective, or because they occur in proteins that are never encountered by cells that recognize the LRE motif.

Most of the proteins known to promote adhesion through an RGD-dependent mechanism are devoid of LRE, including fibronectin, vitronectin, and collagen IV. However, three RGD-containing proteins also contain LRE, namely Von Willibrand's Factor, tenascin, and the A chain of laminin. LRE also is contained within one member of the immunoglobulin superfamily, myelin-associated glycoprotein, but is not found in several other (e.g. NCAM, L1 and thy-1, or in the calcium-dependent adhesion molecules N-, P-, and E-cadherin.

Published sequences for acetylcholinesterase contain an LRE sequence. The LRE sequence also is found in members of 3 of the 5 classes of intermediate filament proteins: vimetin, desmin, and GFAP (type III) all contain 3 LRE sequences; several neurofilaments (type IV) contain 2 LRE sequences; and a laminin (type V) contains 1 LRE sequence.

Notwithstanding the presence of the LRE sequence in published sequences of adhesive and other proteins, no prior suggestion has pointed to this small tripeptide sequence as constituting a motor neuron-selective adhesive site as defined herein.

The blocking of cell attachment to s-laminin is illustrated herein with several short synthetic peptides of 3 to 21 amino acids long which contain the LRE sequence as a minimum essential sequence. The dipeptides LR and RE were inactive as were larger peptides within the 21 amino acid sequence that did not contain the LRE sequence.

Thus, inhibitory activity is demonstrated with the full 21 amino acid long fragment that begins 121 amino acids from the C-terminus of s-laminin, namely:

AEKQLREQVGDQYQTVRALAE.

Similar activity is demonstrated with illustrative peptide fragments thereof which contain the essential tripeptide sequence LRE:

AEKQLREQVGD,

KQLREQ,

LREQVG,

LREQ, and

LRE

On the other hand, inhibiting activity is not shown with other peptide fragments thereof which did not contain the tripeptide sequence LRE:

AEKQLR,

EQVGDQYQTV and

QYQTVRALAE.

It will be appreciated that other short peptides having inhibitory activity toward attachment of motor neurons to s-laminin can be synthesized by incorporating the aforesaid essential tripeptide sequence LRE in other combinations of amino acids.

DETAILED DESCRIPTION OF THE INVENTION

While the specification concludes with claims particularly pointing out and distinctly claiming the subject matter regarded as forming the present invention, it is believed that the invention will be better understood from the following description taken in connection with the accompanying drawings in which:

FIG. 1 shows in two panels (a) and (b) the production and immunoreactivity of s-laminin fusion proteins. The s-laminin cDNA clones RK36 and RK65-6 were ligated into the high-efficiency translation vector pET and fusion proteins were produced as described hereinafter. Panel (a). Purification of a fusion protein; SDS-polyacrylamide gel stained for total protein with Coomassie Brilliant Blue. Lane 1, bacterial proteins from BL2I-DE3 cells containing pET-RK36, before induction; lane 2, after induction; lane 3, fusion protein purified from the induced bacteria. Panel (b). Immunoreactivity of pET-RK36 (lane 1)O and pET-RK65≢(lane 2) fusion proteins; immunoblot of induced bacterial lysates probed with anti-s-laminin monoclonal antibody, D5 (Hunter et al., supra.). In both a and b- a volume equivalent to 50 μl of bacterial culture was applied to each lane. Arrows indicate molecular weight standards of 200, 116, 80, 68, 29, and 14 kb (myosin, β-galactosidase, transferrin, BSA, carbonic anhydrase, and lysozyme). pET-RK36 and pET-RK65-6 proteins have a $M_r$s of ~20K and ~80K, respectively, consistent with the deduced amino acid sequence of the cDNAs. Upper immunoreactive b and in b2 is ~160 kD, and may represent an incompletely reduced dimer.

FIG. 2 shows the adhesion of ciliary ganglion neurons to fusion proteins. The locations of s-laminin fusion proteins are shown relative to the entire deduced amino acid sequence of s-laminin (1766 amino acids). Fusion proteins were produced, and adhesion was assayed, as described hereinafter. Cell attachment activity was scored as positive if the number of neurons adherent to a given substrate was >3-fold higher than the number adherent to BSA. Fusion protein leader sequences are shown as dots (capsid protein) or wavy lines (β-galactosidase); s-laminin sequences are shown as open bars.

FIG. 3 shows a comparison of neuronal attachment to laminin and s-laminin. Substrates were immobilized to tissue culture wells as described hereinafter. Ciliary neurons (a–c) or tectal cells (d–f) were allowed to adhere for 2 hr, wells were washed, and the cells were than fixed and photographed. Ciliary neurons adhere well to laminin (a; 100 μg/ml) and pET-RK36 (b; 10 μg/ml), but not to BSA (c; 30 mg/ml). Tectal cells adhere well to laminin (d), but not to pET-RK36 (e) or BSA (f). Bar is 50 μm.

FIG. 4 shows in three panels (a), (b) and (c) the inhibition of adhesion to pET-RK36 and other substrates by synthetic peptides. (a) The location of the synthetic peptides M1–M9 are shown relative to the deduced amino acid sequence of RK36. (b) Attachment of ciliary neurons to pET-RK36 was assayed in the presence of peptides M1–M9 (200 μg/ml). Only peptide M5 significantly inhibited adhesion. (c) M5 or M7 (200 μg/ml final concentration) was mixed with ciliary neurons which were plated on nitrocellulose that had been coated with pET-RK36 (10 μg/ml), laminin (100 μg/ml), concanavalin A (100 μg/ml), or poly-L-lysine (100 μg/ml). M5 selectively inhibits adhesion to the s-laminin fragment. b and c show data from representative tests; each assay was repeated 4–6 times.

FIG. 6 shows the location of LRE sequences in laminin and s-laminin. Domain structures and their diagrammatic representations are adapted from Sasaki et al., *J. Biol. Chem.* 262, 17111–17117 (1987); Ibid. 263, 6536–16544 (1988); *Proc. Natl. Acad. Sci. USA* 84, 935–939 (1987). The 3 LRE sequences in s-laminin, the 2 LRE sequences in laminin B2, and the single LRE in laminin A are marked with open arrows. The neurite outgrowth promoting site of laminin is thought to lie within or near the "25K" region of the "E8" fragment [Martin and Timpl, *Ann. Rev. Cell Biol.* 3, 57–85, (1987) and Edgar et al., *J. Cell Biol.* 106, 1299–1306 (1988)]. The motor neuron attachment site in the s-laminin RK36 fragment overlaps the position of laminin's "25 K" fragment.

The novel inhibitory peptides of this invention can be prepared by known solution and solid phase peptide synthesis methods.

In conventional solution phase peptide synthesis, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group (BOC), various coupling reagents, e.g., dicyclohexylcarbodiimide or carbonyldimidazole, various active esters, e.g., esters of N-hydroxyphthalimide or N-hydroxy-succinimide, and the various cleavage reagents, e.g., trifluoroacetic acid (TFA), HCL in dioxane, boron tris-(trifluoroacetate) and cyanogen bromide, and reaction in solution with isolation and purification of intermediates is well-known classical peptide methodology.

The preferred peptide synthesis method follows conventional Merrifield solid-phase procedures. See Merrifield, *J. Amer. Chem. Soc.* S5, 2149–54 (1963) and *Science* 150, 178–85 (1965). This procedure, though using many of the same chemical reactions and blocking groups of classical peptide synthesis, provides a growing peptide chain anchored by its carboxy terminus to a solid suppor&, usually cross-linked polystyrene, styrenedivinylbenzene copolymer or, preferably, p-methylbenzhydrylamine polymer for synthesizing peptide amides. This method conveniently simplifies the number of procedural manipulations since removal of the excess reagents at each step is effected simply by washing the polymer.

Further background information on the established solid phase synthesis procedure can be had by reference to the treatise by Stewart and Young, "Solid Phase Peptide Synthesis," W. H. Freeman & Co., San Francisco, 1969, and the review chapter by Merrifield in *Advances in Enzymology* 32, pp. 221–296, F. F. Nold, Ed., Interscience Publishers, New York, 1969; and Erickson and Merrifield, *The Proteins*, Vol. 2, p. 255 et seq. (ed. Neurath and Hill), Academic Press, New York, 1976.

Amino acids are shown herein either by standard one letter or three letter abbreviations as follows:

| Abbreviated Designation | | Amino Acid |
| --- | --- | --- |
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

In order to illustrate specific preferred embodiments of the invention in greater detail the following exemplary laboratory preparative work was carried out.

EXAMPLE

Methods

Production of fusion proteins

Figure 1A:
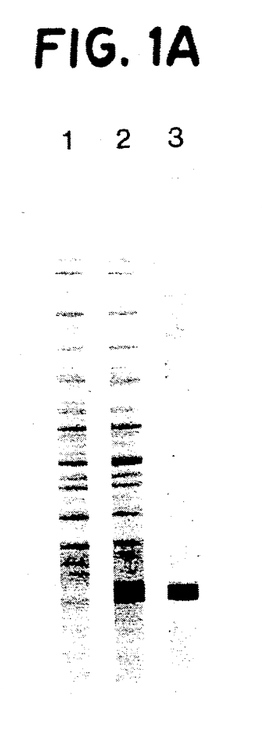
Figure 1B:
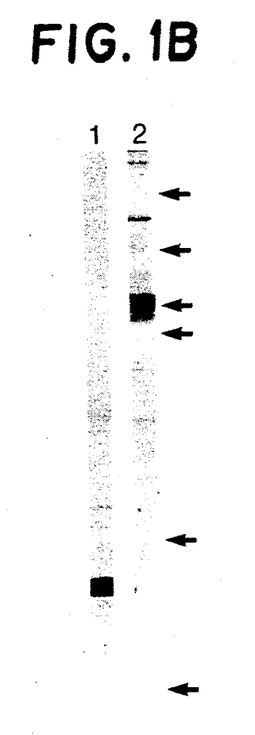

To produce fusion proteins, cDNAs encoding fragments of s-laminin were inserted into the high efficiency expression vector of Resenberg et al., *Gene* 56, 125-135 (1987), as follows. Clones RK36 and RK65-6 were excised from the λgtll vector using EcoRI. Blunt end termini were generated using Klenow polymerase, and the resulting fragments were ligated in frame into pET vectors which had been cut with BamHI and treated with Klenow polymerase. The resultant plasmids were introduced into competent JM109 cells. DNA isolated from individual colonies was used to transform competent BL21-DE3 cells, which support inducible transcription of the pET construct. Colonies were grown at 37° C. to an $OD_{600}$ −1.0, then induced with 0.4 mg/ml isopropylthiogalacto-pyranoside for 3 hr at 37° C. Cells were pelleted and suspended in 0.1 volumes phosphate-buffered saline (PBS: 150 mM NaCl, 15 mM NaPO*, pH 7.2), then frozen, thawed, and sonicated in 0.5% Nonidet ® P-40 nonionic detergent (Sigma, St. Louis, Mo.) in PBS. Inclusion bodies containing the fusion protein were pelleted by centrifugation at 10,000×g for 2 min, then resuspended in 0.1×the original culture volume of PBS and frozen in aliquots. Prior to use, the fusion protein was dissolved by boiling in 5% 2-mercaptoethanol for 3 min; contaminating proteins were pelleted by centrifugation 10,000×g for 1 min. The control pET was prepared in the same manner as pET-RK36 and pET-RK65-6, except that BL21-DE3 cells containing the pET vector alone were induced. FIG. 1 demonstrates the purification achieved by these steps and documents the immunoreactivity of the fusion proteins with a monoclonal antibody to s-laminin.

OTHER SUBSTRATES

Laminin (Collaborative Research; nominally 1.2 mg/ml) was stored in small aliquots at −20° C., and thawed immediately prior to use. Poly-lysine (Sigma, St. Louis, Mo.) was stored as a sterile 100 μg/ml solution in water. Concanavalin A (Sigma) was prepared at 1 mg/ml in PBS. In a few tests, β-galactosidase-s-laminin fusion proteins (Hunter et al, supra.) or a β-galactosidase-intermediate filament fusion produced in the λgtll vector were tested. These vectors were used to infect *E. coli* and bacterial lysogens were prepared as described by Huynh et al., In: *DNA Cloning: A Practical Approach*, D. M. Glover, ed., pp. 49-78, IRL Press, Oxford, (1985). Prior to use, the lysogens were sonicated and centrifuged to remove bacterial debris.

CELL ATTACHMENT ASSAYS

Substrates were immobilized to tissue culture dishes as described by Lagenaur and Lemmon, *Proc. Natl. Acad. Sci. USA* 84, 7753-7757 (1987). Briefly, nitrocellulose (BA85; Schleicher and Schuell, Keene, N.H.) was dissolved in methanol (1 cm²/ml), applied to tissue culture wells (90 μl per 16 mm diameter well) and allowed to dry. Drops (1.5-3 μl) of substrates in solution were applied and allowed to bind for 20 min. after which the drops were aspirated. Nonspecific binding sites on the nitrocellulose were then blocked by incubating wells with the following series of solutions: 10 mg/ml bovine serum albumin (BSA; Sigma) in PBS for ~1 min; 30 mg/ml BSA in PBS for 2-3 hr; Earles' Minimum Essential Medium (MEM) containing 2% fetal bovine serum and 25 mM HEPES, pH 7.4, for 5 min; PBS, twice briefly; and Earles' MEM containing 1 mg/ml BSA and 25 mM HEPES, pH 7.4, for 30 min at 37° C. in a humidified chamber containing 7% $CO_2$. At this point, neurons were added, with or without synthetic peptides, and incubated for 2 hr at 37° C. Finally, the wells were washed twice with PBS pre-warmed to 37° and adherent cells were fixed in place with 2% paraformaldehyde and 2% glutaraldehyde in PBS.

NEURONS

Neurons were dissociated from chick ciliary ganglia as previously described by Nishi and Berg, *Proc. Natl. Acad. Sci. USA* 74, 5171-5175 (1977);

Covault et al., *J. Cell Biol.* 105, 2479-2488 (1987). Each well received ~5000 neurons, which corresponds to ~1 E8 ganglia, ~1.5 E10 ganglia, and ~2 E13 ganglia (E8, E10 and E13 are stages of development of the embryonic chick) [neuronal death is occurring over this time course; Landmessen and Pilar, *J. Physiol.* 241, 715-736 (1974)]. Chick dorsal root ganglia and optic tecta were dissociated in the same manner; each well received cells from 4-5 dorsal root ganglia or 0.25 optic tecta. For B35 and B104 cell lines, each well received 20,000 cells. For PC12 cells, each well received 5000 cells. In some tests, PC12 cells were grown with 50 ng/ml nerve growth factor (NGF) for 3-6 days before use. All cells were suspended in Earles' MEM containing 1 mg/ml BSA and 25 mM HEPES, pH 7.4, for addition to tissue culture wells.

PEPTIDES

Peptides were synthesized by the Merrifield solid-phase method on an Applied Biosystems Model 430A peptide synthesizer at a 0.5 mmole scale. A p-methylbenzhydrylamine resin was employed for peptide amides and a phenylacetamidomethyl resin for peptide acids. Coupling of appropriate Boc-amino acids was performed using dicyclohexylcarbodiimide/hydroxybenzotriazole coupling cycles as recommended by the manufacturer. Peptides were removed from the resin and treated with hydrogen fluoride/anisole/dimethyl sulfide. Purification to >90% purity was accomplished by high pressure liquid chromatography, using either a Vydac C-18 reverse phase column (Separations Group) or a μBondapak column (Waters) with gradients of 0.30% acetonitrile containing 0.05% trifluoroacetic acid. Lyophilized peptides were dissolved at 10 mg/ml in sterile water and the pH was adjusted to 7; aliquots of these stock solutions were diluted into medium directly before each test.

RESULTS

Motor neurons adhere to a C-terminal fragment of s-laminin

Figure 2:
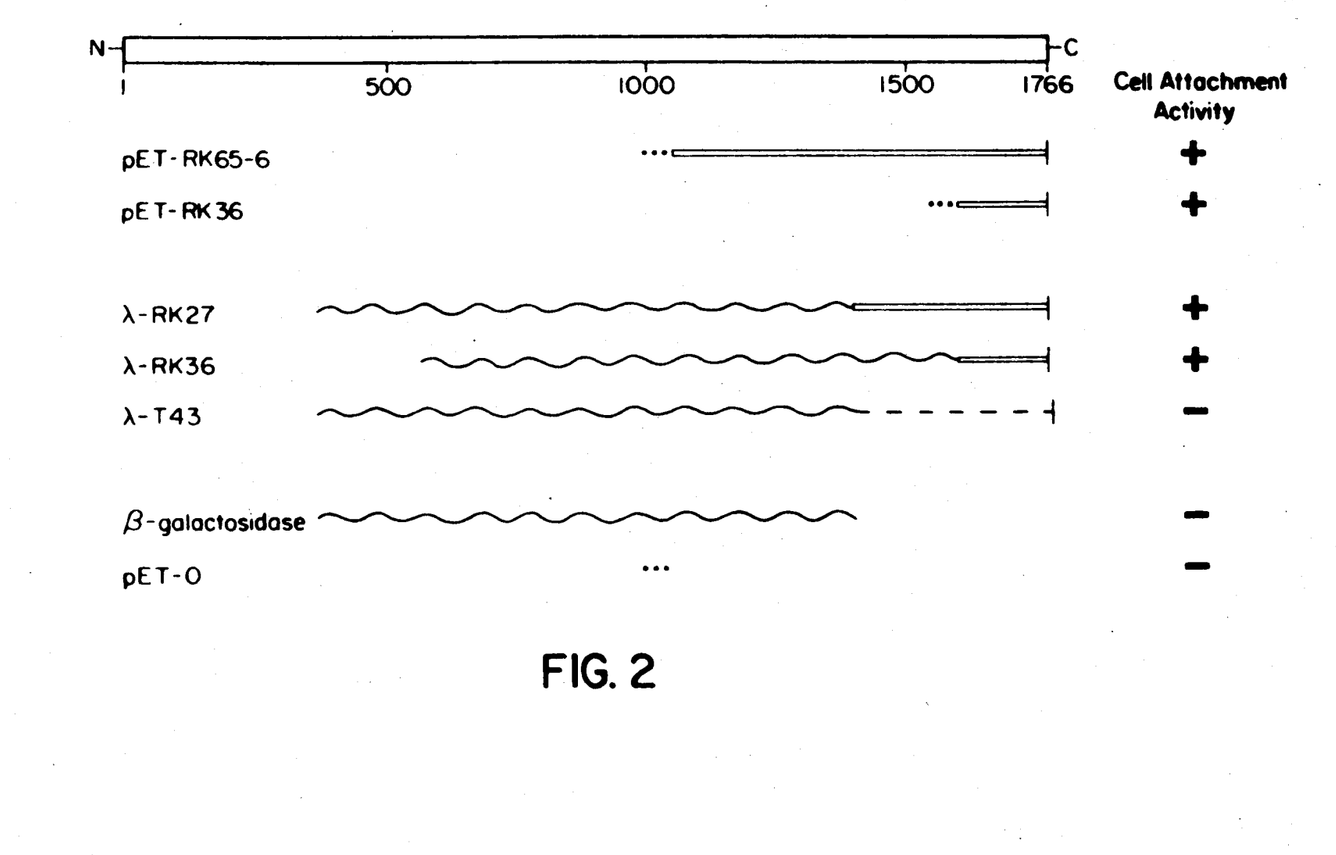
Figure 3:
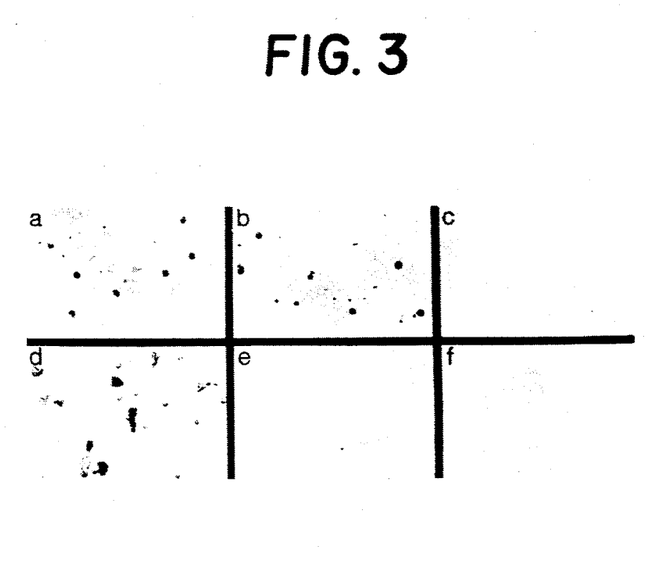

It has been previously shown that neurons from embryonic chick ciliary ganglia adhere to a recombinant protein that consists of the C-terminal 40% of s-laminin fused to a 10 amino acid fragment of a phage capsid protein (Hunter et al., supra.). Initially, to localize the adhesive site more precisely, a second fusion protein, pET-RK36 (FIG. 1), which contains only the C-terminal 20 kd of s-laminin was tested herewith. (FIG. 2). During a 2 hour assay of cell attachment, ~30-40% of the applied ciliary neurons adhered to nitrocellulose that had been coated with optimal concentrations of laminin of the 20kd s-laminin fragment and then blocked with BSA (FIG. 3a, b); <2% the neurons adhered to nitrocellulose that had been coated with BSA alone (FIG. 3c). Significant adhesion to s-laminin was observed with as little as 1 μg/ml in solution; adhesion to laminin was seen with as little as 20 μg/ml. Maximal adhesion was obtained when solutions ~10 μg/ml s-laminin or ~500 μg/ml laminin were applied to the nitrocellulose. These optimal concentrations are similar in molar terms (~0.5 μM; Mr is ~900,000 for laminin and ~20,000 for the s-laminin fragment). Thus, although it is not known what fraction of applied proteins actually bind to the nitrocellulose, laminin and the s-laminin fragment appear to be similarly adhesive for ciliary motor neurons.

To ensure that the adhesion to fusion proteins was attributable to sequences in s-laminin, rather than to vector-encoded sequences or to bacterial proteins, attachment to several other recombinant proteins was tested (FIG. 2). Ciliary neurons attached to bacterial extracts enriched in the protein λ-RK36, which comprises the 20kd RK36 fragment fused to E. coli β-galactosidase, as well as λ-RK27, which comprises the 40 kd C-terminal fragment fused to β-galactosidase. In one test, the λ-RK36 protein was partially purified by size exclusion chromatography; the partially pure protein remained active in the adhesion assay. In contrast, no significant attachment was detected to a β-galactosidase fusion protein that contained no s-laminin sequences (λ-T43), to pure β-galactosidase, or to an extract from E. coli transformed with pET-O, which encodes the capsid protein leader sequence. These results supported the initial conclusion that an adhesive site for ciliary neurons is contained within the C-terminal 10% of s-laminin.

The C-terminal adhesive site on s-laminin is selective for motor neurons

Ciliary neurons were selected for initial tests because many of these neurons normally form neuromuscular junctions on striated muscle fibers in vivo [Pilar et al., J. Neurophys. 43, 233–254 (1980)]and are, therefore, somatic motor neurons. In addition, it had been shown previously that processes of ciliary neurons recognize original synaptic sites on adult rat muscle fibers in an in vitro bioassay [Covault et al., J. Cell Biol. 105, 2479–2488, (1987)]. To extend these tests, it was determined whether neurons of other types also adhered to the s-laminin fragments. Neurons were dissociated from dorsal root ganglia, optic tecta, and ciliary ganglia of E10 chick embryos. Dorsal root ganglia contain a pure population of sensory neurons, all of which are postmitotic by E7.5 [Carr and Simpson, J. Comp. Neur. 182, 727–740 (1978)]. The optic tectum contains several classes of interneurons and projection neurons, all of which are born by E9 [LaVail and Cowan, Brain Res. 28, 421–441 (1971)]. In addition, cells of the rat brain-derived, neuron-like cell lines B35 and B104 [Schubert et al., Nature 249, 224–227 (1974); J. Neurosci. 6, 2829–2836 (1986)], and the rat pheochromocytoma cell line, PC12, were tested. Following treatment with NGF, PC12 cells express several features of adrenal chromaffin cells and/or sympathetic neurons [Tischler and Greene, Nature 258, 341–342 (1975)]. Both mitotically active PC12 cells grown in the absence of NGF and cells that had been grown in the presence of NGF to induce their differentiation were tested. Thus, this panel of cells enabled comparison of the behavior of motor neurons with that of sensory neurons, central neurons, dividing neuroblasts, and sympathetic-like cells.

Results of this comparison are summarized in Table 1, below, and some examples are shown in FIG. 3. Far more tectal cells, sensory neurons, B35 and B104 cells, dividing PC12 cells, and differentiated (NGF-treated) PC12 cells adhered to laminin than to the s-laminin fragments pET-RK36 and pET-RK65-6. For tectal, B35, B104, and PC12 cells, adhesion to the s-laminin fragments was not significantly above background level for the assay. A few more neurons did adhere to the s-laminin fragments than to BSA-coated nitrocellulose, but at least 10-fold more cells adhered to laminin than to s-laminin. Thus, the 20kd C-terminal fragment of s-laminin contains a site that is adhesive for motor neurons.

Recent studies of retinal [Cohen et al., Nature 322, 465–467 (1986); Hall et al., J. Cell Biol. 104, 623–624 (1987)]and ciliary ganglion cells [Tomaselli and Reichardt, J. Neurosci. Res. 21, 275–285 (1988)]have indicated that the responsiveness of neurons to extracellular matrix molecules, including laminin, is developmentally regulated. It therefore seemed possible that the attachment of ciliary neurons to s-laminin reflected a stage-specific, rather than a cell type-specific, response. Therefore ciliary neurons from E8, E9, E10, E11 and E13 embryos were tested in the adhesion assay; this interval encompasses the time of naturally occurring cell death and a period when many synapses form [Landmesser and Pilar, J. Physiol. 241, 715–736 (1974)]. At each age tested, similar numbers of neurons adhered to s-laminin and to laminin. At each stage, 30–50% more neurons adhered to poly-lysine (a substrate to which most neurons adhere non-specifically) than to either laminin or s-laminin, consistent with previous reports that some ciliary neurons are poorly responsive to laminin (Tomaselli and Reichardt, supra.). Nevertheless, it is evident that ciliary neurons of several ages are capable of attachment to s-laminin.

A short s-laminin-derived peptide can promote or inhibit cell attachment

Figure 4A:
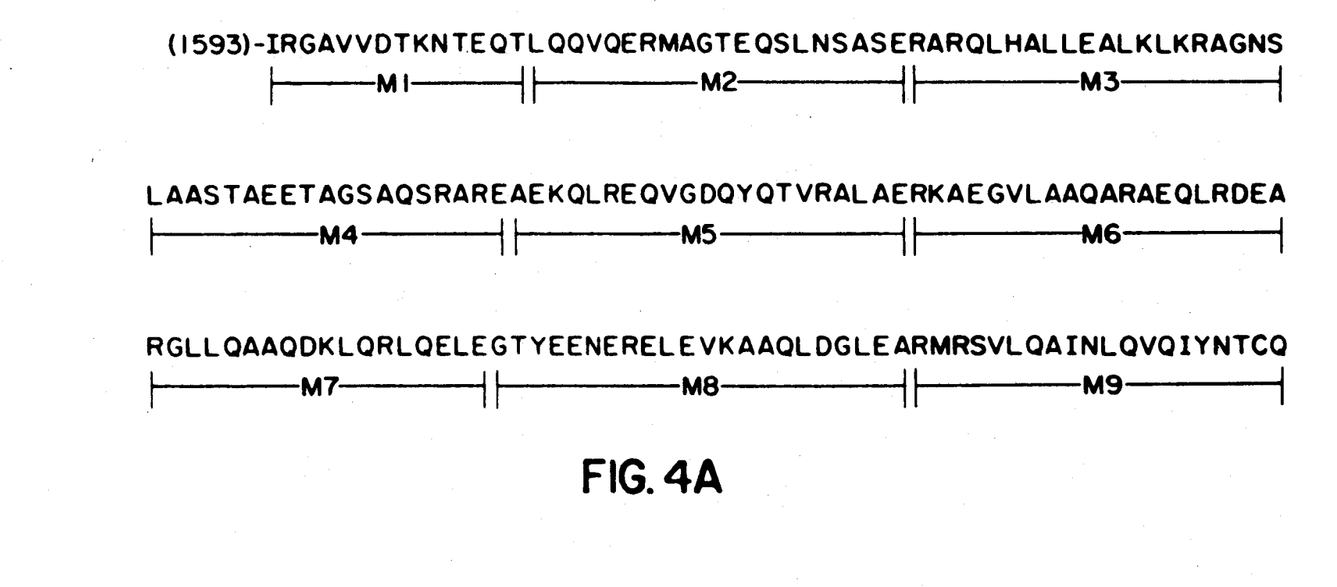
Figure 4B:
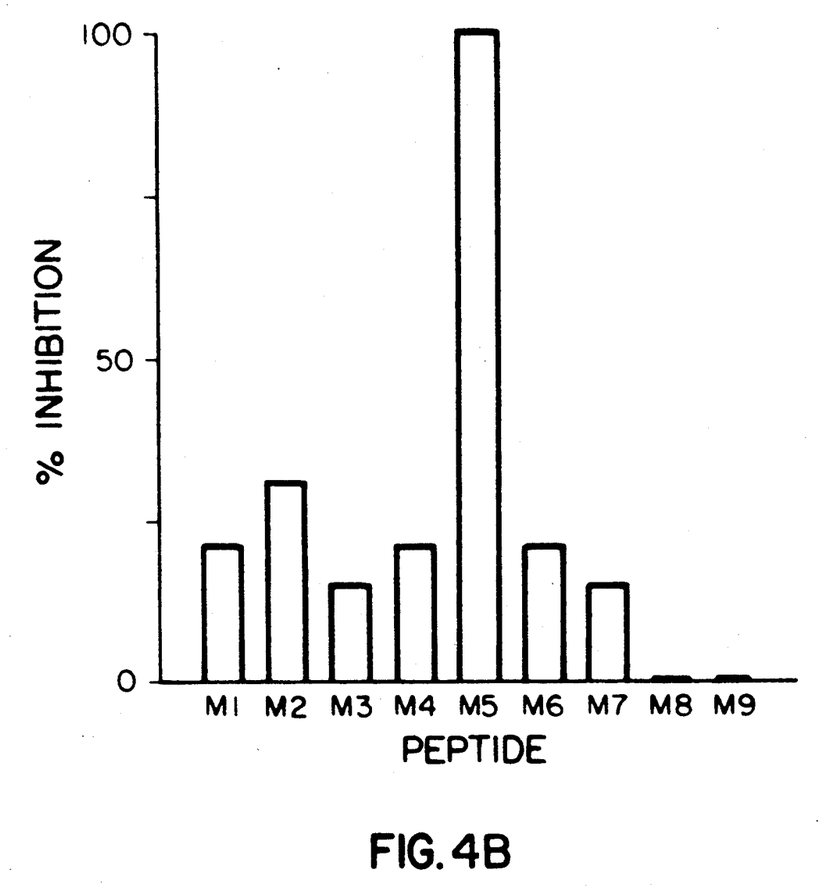

In order to determine short peptide sequences which effectively inhibit the binding of motor neurons to s-laminin, 9 peptides (M1–M9) to span the 20kd adhesive domain encoded by the cDNA clone, RK36 (FIG. 4a), were synthesized. These peptides were added to culture medium and tested for their ability to inhibit adhesion of ciliary neurons to substrata coated with the pET-RK36 s-laminin fragment. At concentrations of 200 μg/ml, only peptide M5 significantly inhibited adhesion to s-laminin (FIG. 4b). This result suggested that a neuronal receptor for s-laminin recognized a sequence contained partially or entirely within the M5 sequence; soluble M5 would then act by binding to this receptor and blocking adhesion to the substratum.

Figure 4C:
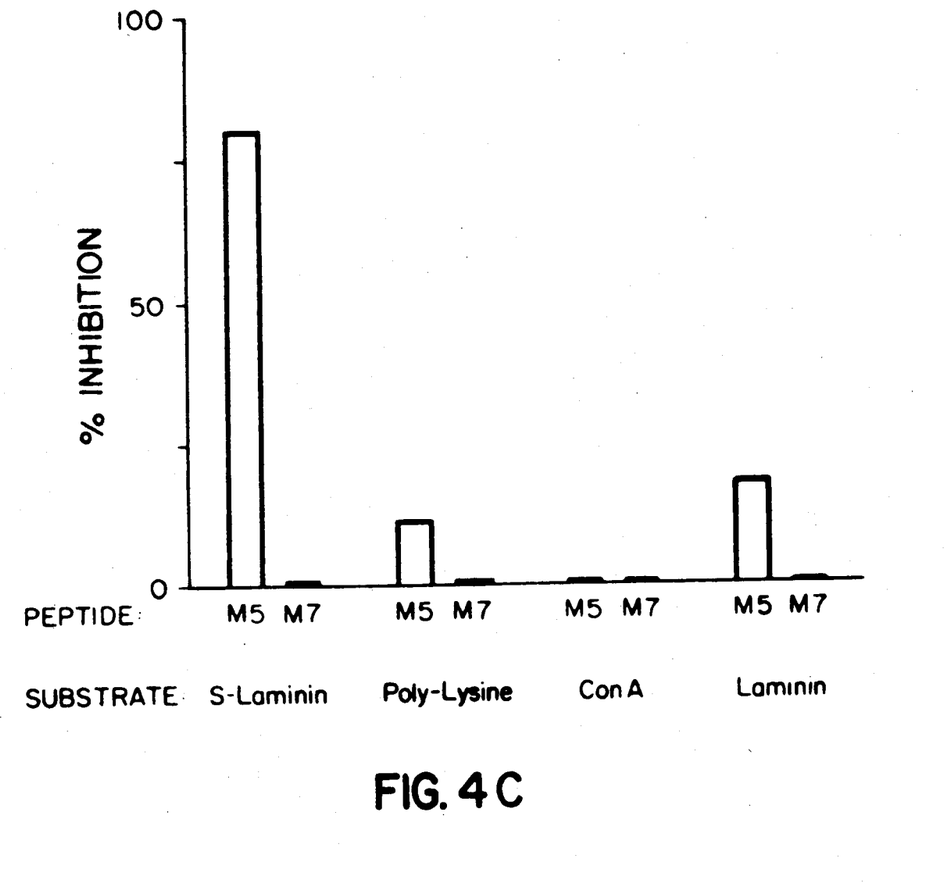
Figure 5:
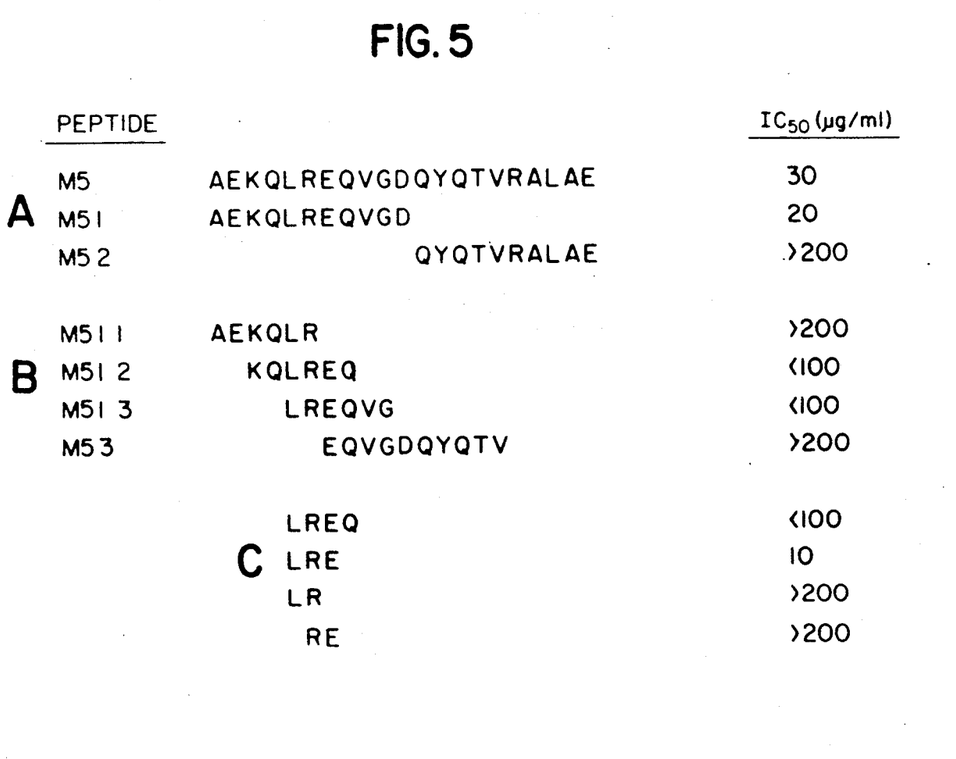
FIG. 5 shows in four panels (a), (b), (c) and (d), the inhibition of neuronal adhesion to pET-RK36 by synthetic peptides. (a-c) Concentrations of peptides that inhibited adhesion by 50%. The amino acid sequences of the peptides used are shown relative to M5. The position of M5 within RK36 is shown in FIG. 4a, and the position of RK36 within s-laminin is shown in FIG. 2. Peptides M5-12, M5-13, and LREQ were not tested at concentrations of <100 μg/ml. (d) Dose-response curves for the inhibition of adhesion to pET-RK36 by synthetic peptides M5, M51, and LRE, expressed in molar terms. IC$_{50}$ for all three peptides is 10–20 μM.
Figure 5D:
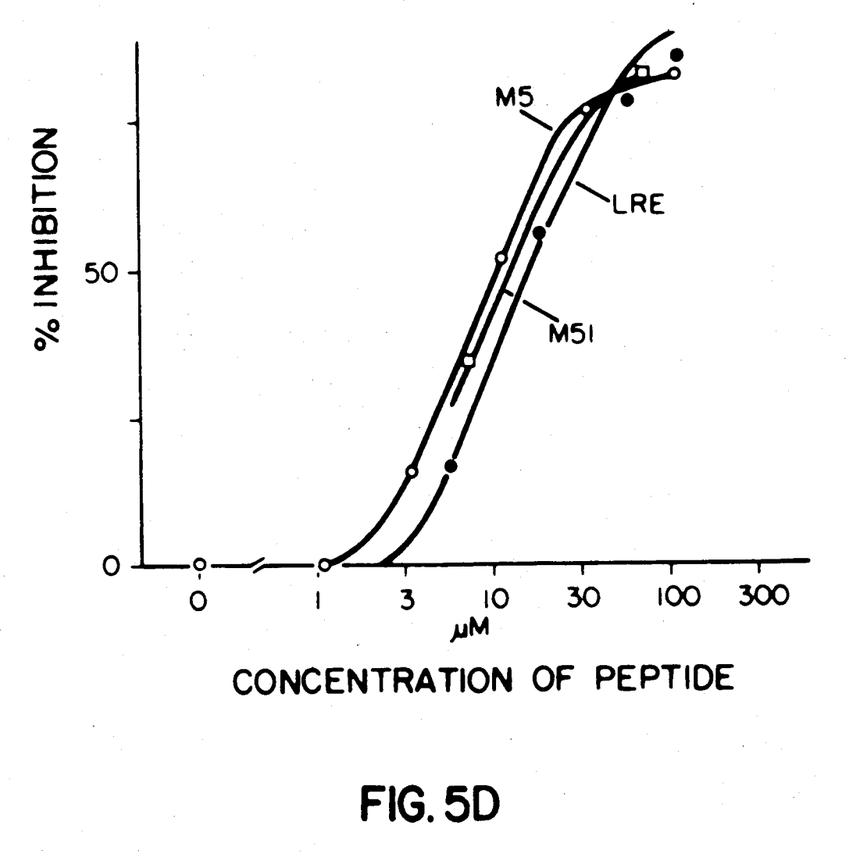
Figure 6:
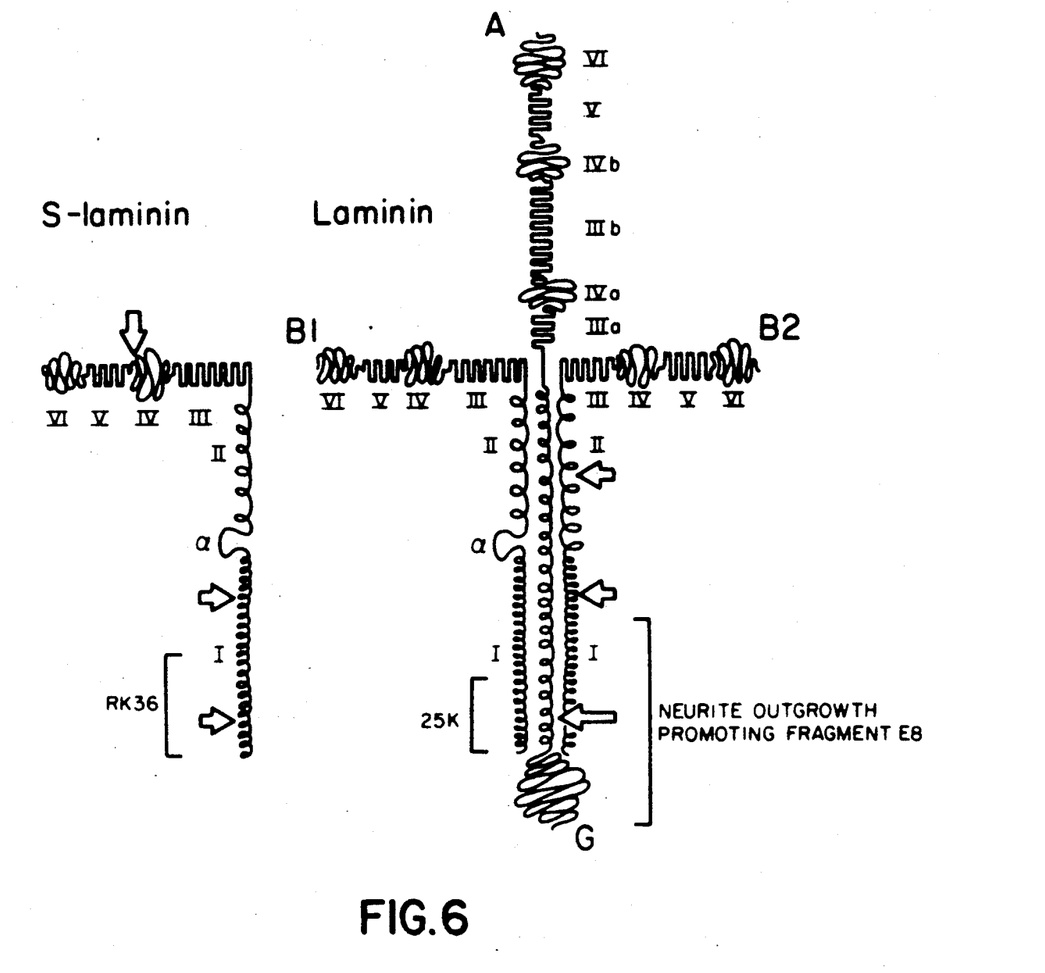

Before accepting this conclusion, however, it was necessary to test two alternative possibilities. The first was that M5 affected neuronal viability or adhesiveness generally. To test this possibility, it was determined whether M5 was capable of inhibiting the attachment of neurons to other adhesive substrata. As shown in FIG. 4c, 200 μg/ml M5 did not significantly inhibit the adhesion of ciliary neurons to concanavalin A or poly-lysine. M5 did inhibit adhesion to laminin significantly, but only partially and at high concentrations (~20% inhibition at 200 μg/ml and 25% at 500 μg/ml). This is in marked contrast to the inhibition of adhesion to s-laminin, which is nearly complete at 100 μg/ml (see FIG. 5d, below); it may reflect nonspecific effects, or the presence of similar adhesive domains in laminin. Thus, the inhibition of cell attachment to s-laminin by M5 is selective both for the peptide and for the substratum. The second possibility was that the synthetic peptide was capable of interacting selectively with neurons, but did not itself comprise and adhesive sequence. Therefore, the ability of M5 and other s-laminin-derived peptides to promote, rather than to inhibit, cell attachment, was assayed. Peptides were immobilized on nitrocellulose, and attachment of neurons to the substrate measured a before. Little specific adhesion was observed at peptide concentrations of ≦1 mg/ml, consistent with previous reports [(e.g., Pierschbacher and Rouslahti, Nature 369, 30-33, (1984)]that short peptides adhere poorly to substrata. However, at 10 mg/ml, M5 promoted significant cell attachment, whereas the nearby sequences M3 and M7 did not (Table 2, below). This result provides direct evidence that an adhesive domain in s-laminin is located within a 21 amino acid stretch that begins 101 amino acids from its C-terminus.

Motor neurons recognize a tripeptide sequence in s-laminin

In order to determine the shortest essential peptide sequence within the M5 sequences, to inhibit the binding of motor neurons to s-laminin, successively shorter peptides were synthesized and tested for their ability to inhibit neuronal adhesion to pET-RK36. Two peptides, each of which spans roughly half of M5 (FIG. 5a) were tested first. The peptide containing the N-terminal 11 amino acids of M5, M51, was inhibitory (IC$_{50}$ ~20 μg/ml), whereas the peptide containing the C-terminal 10 amino acids, M52, was inactive at concentrations up to 200 μg/ml. Overlapping peptides that spanned M51 and extended into M52 were then tested. The second and third of these (M512 and M513) were inhibitory, while the first and fourth (M511 and M513) were not (FIG. 5b). These results suggested that the active site lies within the 4 central residues of the M51 sequence (LREQ), while the first four (AEKQ) and final three (VGD) residues are not essential. Therefore, the tetrapeptide, LREQ, and the tripeptide, LRE, were tested as inhibitors of adhesion. Both peptides were active, whereas the dipeptides, LR and RE, were inactive (FIG. 5c). Thus the minimum sequence of an adhesive site in s-laminin is LRE.

The dose-response curves for the inhibition of adhesion to s-laminin by the peptides M5, M51, and LRE are compared in FIG. 5d. Expressed in molar terms, the three curves are virtually indistinguishable, and the IC$_{50}$ for M5, M51, and LRE all lie between 10 and 20 μM. This similarity suggests that the residues of s-laminin that directly flank LRE do not greatly affect the ability of LRE to inhibit the interaction of neurons with the adhesive site.

TABLE 1

Attachment of neurons and neuron-like cells to laminin and to s-laminin fragments.

| Cell Type | SUBSTRATUM | | |
|---|---|---|---|
| | laminin | pET-RK65-6 | pET-RK36 |
| Series A | | | |
| E1O Ciliary ganglion neurons | + | + | + |
| E1O Dorsal root ganglian neurons | + | ± | ± |
| E1O Tectal neurons | + | – | – |
| B35 cells | + | N.D. | – |
| BI04 cells | + | N.D. | – |
| PC12 cells (–NGF) | + | – | – |
| PC12 cells (+NGF) | + | N.D. | – |
| Series B | | | |
| E8 Ciliary ganglion neurons | + | + | + |
| E9 Ciliary ganglion neurons | + | N.D. | + |
| E9 Ciliary ganglion neurons | + | + | + |
| E11 Ciliary ganglion neurons | + | N.D. | + |
| E13 Ciliary ganglion + neurons | + | + | |

Cell attachment assays were performed as described hereinbefore.
"+" indicates 10 times more cells attached to the substratum than to control (BSA).
"±" indicates attachment 1-2X above control.
"–" indicates attachment indistinguishable from control.
"N.D.", not done.
For each cell type, 20 of the cells applied adhered to laminin.

TABLE 2

Attachment of ciliary neurons to s-laminin-derived peptides.

| Peptide | n | Neurons per Field |
|---|---|---|
| M3 | 7 | 5.0 ± 1.7 |
| M5 | 7 | 26.3 ± 3.1 |
| M7 | 9 | 6.8 ± 1.3 |

The peptides, whose sequences are shown in FIG. 4a, were applied to nitrocellulose at 10 mg/ml. Cell attachment assays were performed as described hereinbefore. Values given are means ±S.E.

Various other examples will be apparent to the person skilled in the art after reading the present disclosure without departing from the spirit and scope of the invention. It is intended that all such other examples be included within the scope of the appended claims.

What is claimed is:

1. A novel peptide having inhibitory activity toward the binding of motor neurons to s-laminin in vitro selected from the group consisting of

AEKQLREQVDQYQTVRALAE and fragments thereof containing the essential sequence LRE.

2. The peptide of claim 1 having the sequence LRE.
3. The peptide of claim 1 having the sequence LREQ.
4. The peptide of claim 1 having the sequence LREQVG.
5. The peptide of claim 1 having the sequence KQLREQ.
6. The peptide of claim 1 having the sequence AEKQLREQVGD.

* * * * *